United States Patent [19]

Been

[11] 4,176,706
[45] Dec. 4, 1979

[54] APPARATUS AND METHOD FOR MAKING BRIDGEWORK

[76] Inventor: Larry C. Been, 4335 Bonham, Dallas, Tex. 75229

[21] Appl. No.: 811,427

[22] Filed: Jun. 29, 1977

[51] Int. Cl.$^2$ .......................... B22C 9/04; A61C 13/22
[52] U.S. Cl. ........................................ 164/34; 433/200
[58] Field of Search ............................ 32/5, 6, 8, 9, 2; 164/34

[56] References Cited

U.S. PATENT DOCUMENTS

| | | | |
|---|---|---|---|
| 1,407,557 | 2/1922 | McVicker | 32/9 |
| 1,465,473 | 8/1923 | Hansen | 32/6 |
| 1,523,569 | 1/1925 | Wilson | 32/8 |
| 1,742,310 | 1/1930 | Floyd | 32/9 |
| 2,087,047 | 7/1937 | Scheven | 32/5 |
| 2,196,505 | 4/1940 | Morton | 32/6 |
| 2,315,669 | 4/1943 | Tamarin | 32/9 |
| 2,431,086 | 11/1947 | Saffir | 32/8 |
| 3,971,133 | 7/1976 | Mushabac | 32/2 |

Primary Examiner—Roy Lake
Assistant Examiner—John S. Brown
Attorney, Agent, or Firm—Richards, Harris & Medlock

[57] ABSTRACT

The specification discloses a tooth-shaped member including a central insert which is removable from a facing in order to make the supporting framework for a dental bridge. An appropriate size and shape of a tooth-shaped member is selected and aligned in a gap between built up wax crowns of abutment teeth. The insert extends across the facing and is adhesively bonded at the ends thereof to the adjacent wax crowns. The facing is then removed from the insert. The wax crowns are cut down to the desired shape and the insert and crowns are removed as a single unit. The unit is then cast to form a bridge framework which is coated with porcelain to form artificial teeth.

3 Claims, 13 Drawing Figures

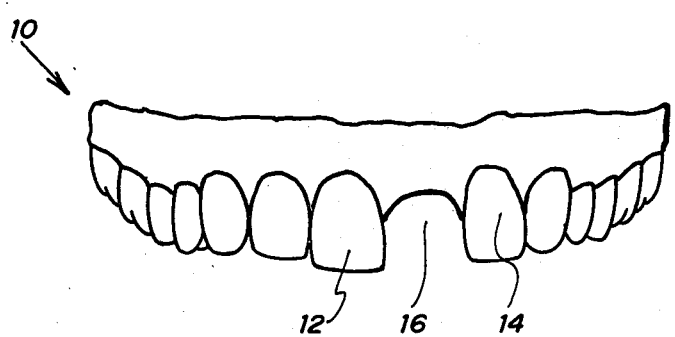
FIG. 1
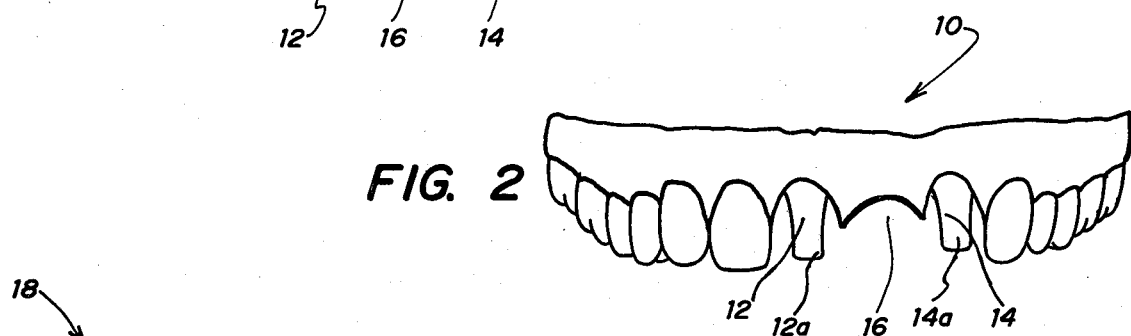
FIG. 2
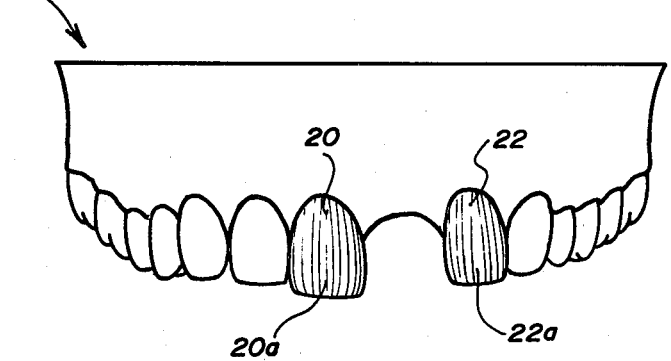
FIG. 3
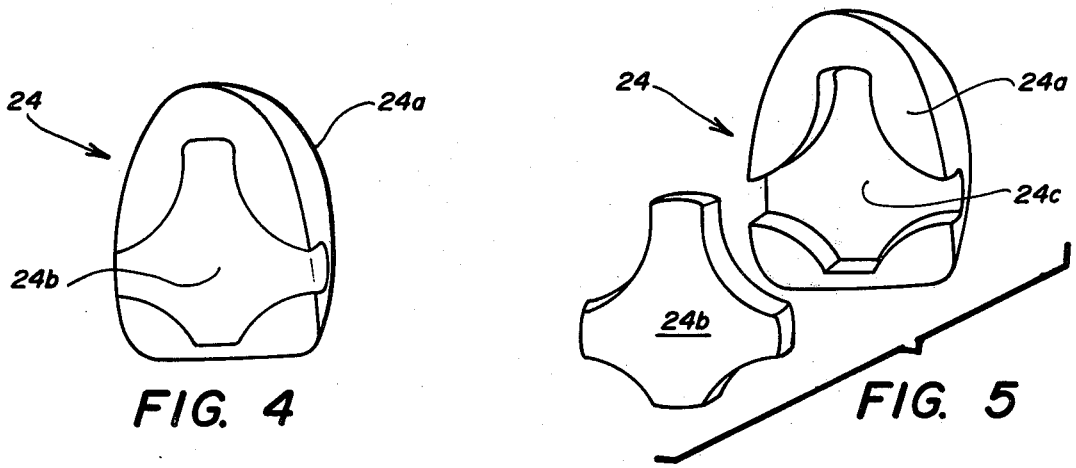
FIG. 4
FIG. 5
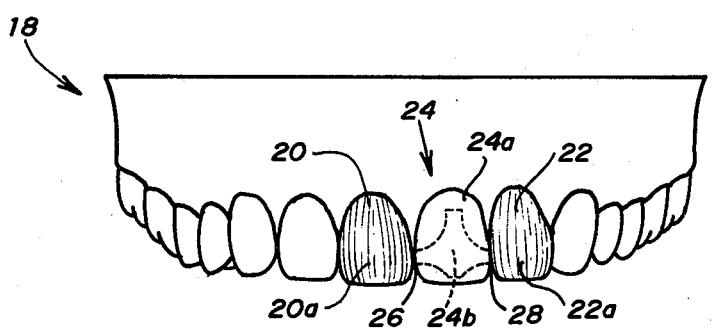
FIG. 6

APPARATUS AND METHOD FOR MAKING BRIDGEWORK

FIELD OF THE INVENTION

This invention relates to dental bridgework and more particularly to the forming of a bridge framework.

THE PRIOR ART

A common procedure which has heretofore been used for forming a dental bridgework includes first forming an impression of the pontic area followed by making a die that simulates the patient's teeth. Wax patterns are then built up on the abutment teeth of the die and an appropriately sized standard wax tooth is inserted and attached within the pontic gap to the wax patterns. The wax pattern abutment build-ups and the wax tooth are then cut down to form a wax model of the metal framework for the resulting bridge. This cut down wax model is then removed from the die and used to produce a metallic casting. Procelain teeth are then formed on the metallic casting to create the resulting bridge.

Problems have occurred in such prior procedures in providing accurate alignment of the teeth forming the bridgework. The cutting down of the standard wax tooth to produce the model of the metallic framework member is a very delicate manual procedure and sometimes the position of the standard wax tooth relative to the abutment teeth is altered by the cutting procedure. Further, the standard wax tooth must be very carefully cut down to provide the strength and uniformity essential to the functional operation and esthetics of the bridge, as well as providing a minimal volume to reduce the quantity of precious metal, usually gold alloy, used in forming the bridge framework. With such prior bridgework forming procedures it has often been difficult to properly cut down the standard wax tooth while maintaining the tooth properly aligned with both the adjacent teeth and the opposing teeth in the other arch, while also providing the required strength and minimal volume. Improper alignment of the bridge can cause pain for the patient, improper mastication, and can even possibly damage the natural teeth. Improper strength and excessive volume of the cut down standard wax tooth can result in a weak bridge or an excessively expensive bridge.

It has been heretofore known to utilize false teeth wherein a tooth facing is detachably connected to a support member. Examples of such structure are shown in U.S. Pat. No. 2,253,222 to Bertram and in U.S. Pat. No. 3,315,358 to Brecht. However, such prior techniques have not been adaptable to form primary framework structure for preparing multiteeth bridgework and have not solved the problems inherent in the cutting down of standard wax teeth as noted above.

SUMMARY OF THE INVENTION

In accordance with the present invention there is provided a method and apparatus for substantially reducing required manual cutting of standard wax teeth while providing a properly aligned and structurally sound frame member using a minimum quantity of precious metal.

In accordance with the invention, a dental bridge is provided wherein a tooth-shaped member is used to form a strong, properly aligned bridge framework while reducing the labor required to shape the structure. The member comprises two portions, a removable facing and an insert that extends into contact with the sides of abutment teeth.

In accordance with another aspect of the present method, a die is made from an impression taken of the patient's teeth. Abutment teeth on the opposite sides of a gap to be filled are shaped and then built up with a wax pattern to form crowns that will support the bridge. The present tooth-shaped member of an appropriate size and shape is properly aligned between the wax patterns. The insert is then adhesively bonded on both sides to the wax patterns of the abutment teeth and the facing is removed. The unit comprising the insert and the wax patterns is removed from the die and used as a model in the investment casting process to produce a bridge framework. Porcelain is then added to the framework to form artificial teeth.

In accordance with yet another aspect of the invention, a method of making a frame for a dental bridge is disclosed which uses a die pattern of a patient's teeth which includes a gap formed between abutment teeth. Wax crown patterns are formed on the abutment teeth and a tooth-shaped facing member is inserted between the wax crown patterns. The facing member has a groove on one side which extends between the contact areas of the facing member and contains a removable rigid insert. The ends of the insert are joined to the sides of the wax crown patterns. The facing member is removed from the insert without disturbing the alignment of the insert with the wax crown patterns. The insert and wax crown patterns are removed as a unit; and, for the final step, the insert and wax crown patterns are cast to form a metal frame for the dental bridge.

BRIEF DESCRIPTION OF THE DRAWINGS

For a more complete understanding of the present invention and the advantages thereof, reference is now made to the following detailed description taken in conjunction with the accompanying drawings in which:

FIG. 1 is a front elevational view of an upper arch with an incisor missing;

FIG. 2 is a front elevational view of an upper arch with shaped abutment teeth;

FIG. 3 is a front elevational view of a dental die with built up abutment teeth;

FIG. 4 is a perspective view of an incisor-shaped artificial tooth with an insert according to the present invention;

FIG. 5 is an exploded view of the incisor-shaped artificial tooth of FIG. 4;

FIG. 6 is a front elevational view of a dental die with an artificial tooth according to the invention inserted in the incisor gap;

DETAILED DESCRIPTION OF THE PREFERRED EMBODIMENT

Figure 7:
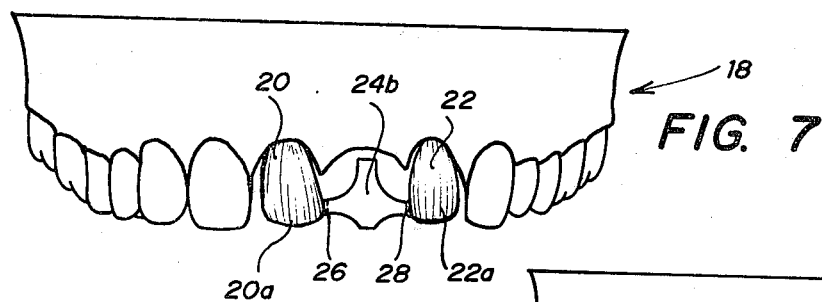
FIG. 7 is a front elevational view of a dental die with the present insert affixed in the incisor gap.

In FIG. 1 there is shown an upper arch 10 with abutment teeth 12 and 14 disposed at opposite sides of the gap 16. Gap 16 is formed by a missing incisor tooth.

In order to install a dental prosthesis or bridgework to compensate for the loss of the incisor from gap 16, the dentist must initially shape the abutment teeth 12 and 14 in order that a bridge structure carrying an artificial replacement tooth can be mounted thereon. As shown in FIG. 2, the abutment teeth 12 and 14 are thus ground and shaped so as to form the supporting structures 12a and 14a.

At this point, the dentist makes an impression of the upper arch 10 as shown in FIG. 2 and from the impression prepares a die made of plaster or like material in the conventional manner. The die is an accurate model of the patient's teeth and gums. The resulting die 18 is shown in FIG. 3 and includes reproductions of abutment teeth 20 and 22. As shown in FIG. 3, a wax pattern 20a is applied to the abutment tooth 20 in order to build up a shape that is desired for the resulting crown on the abutment tooth 20. Likewise, a wax pattern 22a is formed on the abutment tooth 22. The die 18 is waxed and lubricated prior to the attachment of the wax patterns 20a and 22a to allow their later easy removal.

FIG. 4 illustrates an artificial tooth 24 according to the present invention which comprises a rigid insert 24b removably mounted in a groove that is formed in the rear of a facing 21a. Artificial tooth 24 is in the shape of an incisor, but it can be made in the shape of any tooth. The terms tooth and tooth-shaped are used herein to refer to that portion of an actual tooth above the ridge; in other words, the tooth root is not included. Both the facing 24a and the insert 24b can be constructed of a plastic such as an acrylic or other material; however, the insert 24b must be made of a material that is suitable for use in the investment casting process. To be used in this process, the insert must be made of a material which can be dissipated from a mold, through melting or vaporization, after the mold has been heated to a relatively high temperature.

FIG. 5 shows the artificial tooth 24 in an exploded view to illustrate how insert 24b may be removed from facing 24a. Within the facing 24a there is contained a groove 24c formed in a shape to receive the conforming insert 24b with a relatively tight snap fit. Insert 24b has a cross-like shape with horizontal arms which extend across facing 24a, and through each contact area of the facing 24a flush with the side surfaces of the facing 24a. The groove 24c is on the lingual side of the tooth which is the side adjacent the tongue. The term contact area refers to the surface side portion of a tooth that is contiguous an adjacent tooth. The vertical upper and lower prongs of the insert 24b do not extend through either the upper or lower surfaces of the facing 24a. Insert 24b is fitted to slot 24c such that facing 24a can be removed with a slight amount of force.

FIG. 6 illustrates the artificial tooth 24 placed in the gap between the abutment teeth 20 and 22. The facing 24a is chosen from a set of facings of different sizes to fit correctly in the gap. The ends of the horizontal arms of insert 24b, which extend through the side walls of the facing 24a, contact the sides of wax patterns 20a and 22a. If necessary, the facing 24a is ground so that the gingival neck makes proper contact with the ridge. An adhesive 26 is applied to rigidly join the wax pattern 20a to the end of the arm of insert 24b. In a similar fashion, adhesive 28 is applied to rigidly join together the wax pattern 22a and the other end of the arm of insert 24b. An adhesive particularly suitable for this application is DURALAY.

After the insert 24b has been affixed between teeth 20 and 22, the facing 24a is detached and removed from the insert 24b, as shown in FIG. 7. At this stage of the technique, the wax pattern 20a on the abutment tooth 20 is adhesively joined to the insert 24b which in turn is joined to the wax pattern 22a on the abutment tooth 22. By enabling easy removal of facing 24a from 24b, no delicate cutting down of the tooth 24 is required. In addition, the elimination of cutting down reduces the chances of changing the alignment of insert 24b. After the facing 24a is removed, the wax patterns 20a and 22a are cut down with a knife or the like in order to reduce the required metal content of the bridge and to provide space for the porcelain which is to be added to the bridge to form the crowns. With prior art techniques this same cutting down procedure has to be performed on the replacement wax tooth as well; but with the present invention, the cutting down on the replacement tooth is eliminated since the insert is already formed to have the correct shape and thickness.

A serious problem in the production of a bridge frame is the maintenance of proper alignment between the added aritifical tooth 24 and the wax patterns 20a and 22a on the abutment teeth following the cut-down of the wax patterns. This is due to the difficulty in cutting and shaping the wax patterns while they are on the die with the artificial tooth 24 in position, as the space for performing such steps is severely limited. It is much easier to cut and shape the wax patterns 20a and 22a if either they are removed from the die or the artificial tooth 24 is removed from the die. But when any of these members are removed it is possible that the alignment can be lost.

Although it is not necessary in all instances, alignment problems can be overcome by forming a plaster matrix on the outer surfaces of the arch containing the artificial tooth 24 and wax patterns 20a and 22a prior to any cutting or shaping of these wax patterns. The matrix must extend beyond the wax patterns to the teeth adjacent the abutment teeth. After the matrix has hardened, it is removed from the die. The wax patterns 20a and 22a are then detached from the die and are easily cut down to the appropriate shape. After they are shaped, the wax patterns are replaced on the die. The matrix is returned to its position on the die using the teeth adjacent the abutment teeth for alignment. With the matrix thus set, the artificial tooth 24 is positioned against the matrix to return it to its original position in which it was properly aligned. The insert 24b is bonded to the wax patterns 20a and 22a as above described and the matrix is removed. The facing 24a is now removed from the insert 24b.

Figure 8:
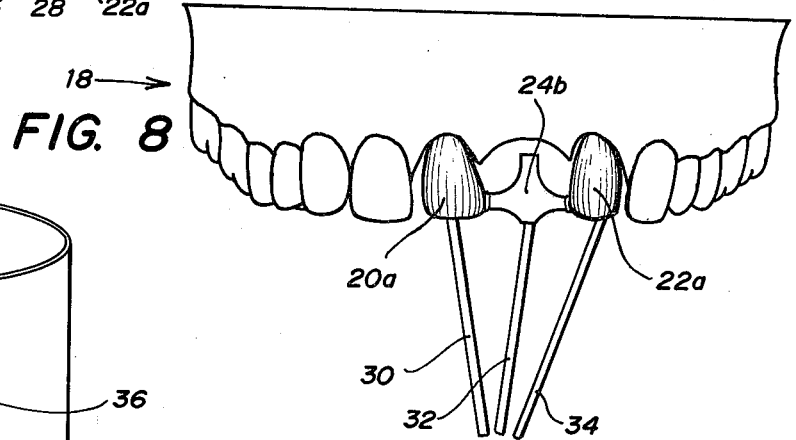
FIG. 8 is a front elevational view of a dental die with sprues attached to the insert and abutment build-ups.

For the next step of the process, sprues 30, 32 and 34 are attached at the ends thereof to wax pattern 20a, insert 24b and wax pattern 22a as shown in FIG. 8. The sprues consist of a relatively rigid sticky wax material which provides support for the model during the forming of the plaster cast and also forms paths for the flow of material into and out of the casting.

Figure 9:
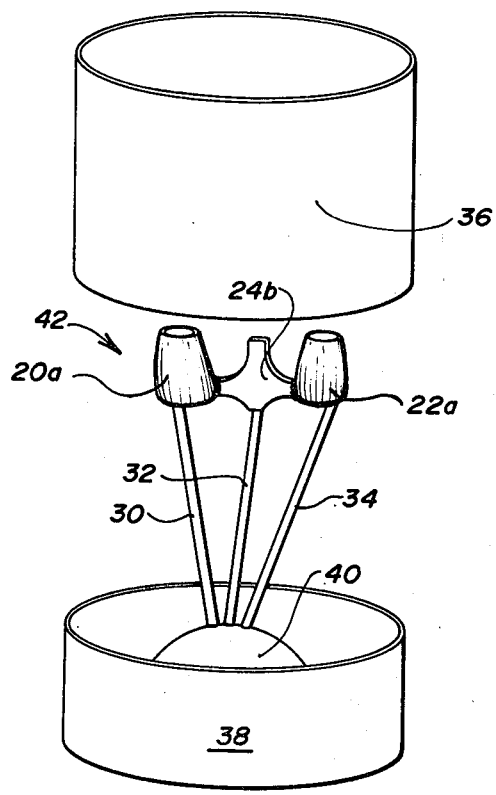
FIG. 9 is a perspective view of a bridge framework about to be mounted in a casting ring.

The model structure 42 comprising the wax pattern 20a, insert 24b, and wax pattern 22a is then removed from the die 18 and the sprues 30, 32 and 34 are attached to a wax support 40 as shown in FIG. 9. The structure 42, which is supported by the sprues 30, 32 and 34, is held in position by the wax support 40 which is disposed within a rubber cap 38. A casting ring 36 is lowered from its position as shown and sealed to the rubber cap 38. A plaster material such as a gypsum compound is poured into the top of the casting ring 36 until the model structure 42 is completely covered. The plaster material is formulated to withstand the high casting temperatures and to have a thermal expansion coefficient that will compensate for the shrinkage of gold alloy as it cools. An alternative material to the gypsum formula is CERAMIGOLD, a mixture which is sold by the Whipmix Company. The casting ring 36, together with its contents, is then placed within a vacuum machine, such as a Vacumat sold by Unitec Corp., where a vacuum is produced to remove any bubbles present in the material. With either casting material, a set up time of approximately thirty minutes is usually required.

After the plaster material within the casting ring 36 has hardened, the rubber cap 38 is removed and the top surface of the plaster is scraped to allow proper ventilation of gases. The casting ring is then placed in a burn-out oven or furnace to remove the model material forming the structure 42 and the sprues 30, 32 and 34. The model material is either melted or vaporized to remove it from the casting. A suitable oven that serves this purpose is manufactured by Unitec Corporation. The plaster cast is heated for a total period of approximately 1½ hours with the temperature reaching 1,300 degrees F.

Figure 10:
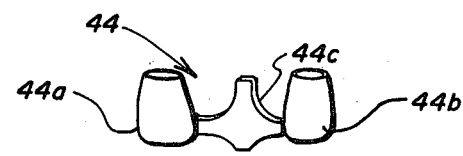
FIG. 10 is a perspective view of a dental bridge framework casting formed in the casting ring of FIG. 9.

The plaster cast is then removed from the oven and placed in a centrifugal casting machine. A gold alloy is melted and placed within a crucible in the casting machine. The machine is then started and the melted alloy is forced by centrifugal force into the casting ring and thence into the casting mold. After the alloy has cooled, the plaster cast material is removed from the metal casting. The cast sprues are detached from the casting, thus forming a rigid gold alloy bridge frame 44 as shown in FIG. 10.

Figure 11:
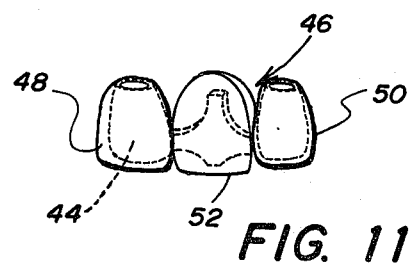
FIG. 11 is a perspective view of a finished bridge formed in accordance with the invention.

Frame 44 includes a pair of crown members, 44a and 44b, separated by a gold alloy replica 44c of the insert 24b. The frame 44 is placed on the abutment teeth 20 and 22 of the die 18 to check for proper alignment and to insure that there is no warpage. Frame 44 is prepared to receive the porcelain coating by rubber wheeling it with a diamond burr and applying a layer of opaque to block the color of the gold. Porcelain is then applied over the opaque with a brush until the porcelain is built up to form the appropriate shape for the replacement teeth. After the porcelain has been applied to form the proper shape, the structure is then fired in a vacuum oven at a temperature of approximately 1,700 degrees F. Next the porcelain is stained if necessary to achieve the proper shade of color and finally the bridge is rubber wheeled and polished. The frame 44 is coated with porcelain to form the finished dental bridge 46 shown in FIG. 11. Bridge 46 includes the crowns 48 and 50 and the artificial incisor tooth 52. The dentist then permanently cements the bridge to the patient's abutment teeth 12 and 14 which have previously been shaped and formed as shown in FIG. 2.

As described above, the present invention was utilized for the replacement of a single missing tooth in a three unit bridge, but the present invention is applicable and particularly useful for bridge structures which are utilized to replace a plurality of missing teeth. With the use of the artificial teeth 24, multiple teeth bridges can be fabricated without severe misalignment problems occuring. And regardless of the number of teeth being replaced, the manual cutting and shaping task is performed only on the two abutment teeth.

Figure 12:
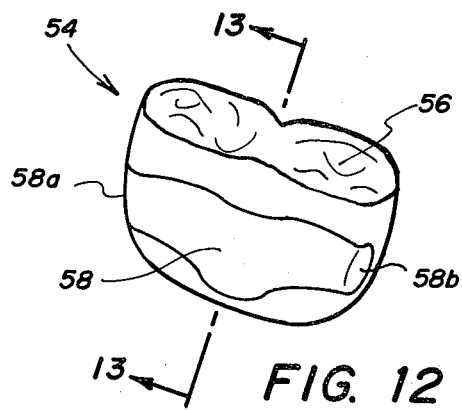
FIG. 12 is a perspective view of a molar-shaped artificial tooth with an insert.

An artificial tooth in the shape of an incisor was used in the process of making the bridge framework as above described. However, the apparatus and procedure is applicable to any tooth such as a molar 54 shown in FIG. 12. FIG. 12 is a view of a molar from the lingual side. A facing 56 is disposed on the buccal side and is removably attached to an insert 58 which extends from one contact area 58a to the other contact area 58b. This facing and insert are used in the same technique as above described for making a dental bridge frame.

Figure 13:
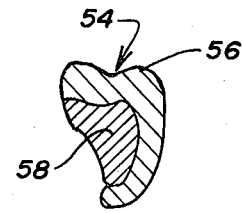
FIG. 13 is a cross section of the artificial tooth with insert shown in FIG. 12.

FIG. 13 shows a cross-sectional view of the artificial molar 54 of FIG. 12. Facing 56 is disposed on the buccal side, while the insert 58 is disposed on the lingual side. Facing 56 is shaped to snugly fit the insert 58, but can be removed without disturbing the alignment of the insert after it has been bonded to the adjacent structures.

It is anticipated that in using the present invention, a dentist or technician will maintain a stock of artificial insert teeth 24 representative of the wide variety of sizes, shapes and types of natural teeth. By using this stock, a proper tooth can be quickly selected for any particular bridge, thereby saving the time previously required to shape and fit the replacement tooth. In additions, after the bridge frame is cast, the facing 24a, which was earlier removed, can be temporarily replaced to be used as a guide in building up the porcelain tooth. In the cases where it is not necessary to grind the facing to fit the bridge, the facing 24a can be fitted with a new insert 24b and reused.

It may thus be seen that the present invention provides a tooth-shaped member having a central insert which is removable from a facing and used to form a frame for a dental bridge. Abutment teeth on a die are built up with wax to the proper shape, and the tooth-shaped member is aligned in the gap between the abutment teeth. The insert is adhesively bonded to the waxed abutments and the facing is removed without disturbing the alignment. The waxed abutments are cut down to allow for a porcelain coating and to reduce the metallic volume. But unlike many prior art techniques, with the present invention there is no cutting or shaping required for the replacement tooth portion of the dental bridge since the insert is previously manufactured to have the correct size, shape and volume for this portion of the bridge framework. Thus, there is a substantial saving of time for a single tooth replacement and a proportional greater time saving for multiple tooth replacements. And, since the inserts of the present invention can be manufactured to precise tolerances even in large quantities, dental frames can now be produced with a consistent high quality not possible with the totally manual procedure of the prior art.

Although various embodiments of the invention have been illustrated in the accompanying drawings and described in the foregoing detailed description, it will be understood that the invention is not limited to the embodiments disclosed, but is capable of numerous rearrangements, modifications and substitutions without departing from the spirit and scope of the invention.

What is claimed is:

1. A method of making a frame for a dental bridge utilizing a die which is a pattern of a patient's teeth including a gap formed between two abutment teeth, which comprises the steps of:

forming a temporary crown pattern on each abutment tooth of the die of a material capable of being dissipated at a temperature below the vaporizing temperatures of metals, inserting between said crown patterns a tooth-shaped facing member having a groove on the lingual side which extends between the contact areas thereof, said groove containing a temporary removable rigid insert formed of a material capable of being dissipated at a temperature less than the vaporizing of metals, joining the ends of said insert to the sides of said crown patterns, removing said facing member from said insert, removing said crown patterns and said insert as a unit from said die, forming a hollow cast by surrounding said unit with casting plaster and dissipating said unit by heating to a temperature below the vaporizing temperature of metals, and casting a metal frame for a dental bridge from said hollow cast.

2. A method of making a frame for a dental bridge as recited in claim 1 further including the step of rubber wheeling said metal frame with a diamond burr to condition the surface of said metal frame.

3. A method of making a frame for a dental bridge as recited in claim 2 further including the step of applying a layer of opaque on said metal frame to block the color thereof.

* * * * *

UNITED STATES PATENT AND TRADEMARK OFFICE
CERTIFICATE OF CORRECTION

PATENT NO. : 4,176,706
DATED : December 4, 1979
INVENTOR(S) : Larry C. Been

It is certified that error appears in the above-identified patent and that said Letters Patent are hereby corrected as shown below:

Col. 3, line 31,   "21a" should be --24a--.
Col. 3, line 41,   after "through" insert --either--.
Col. 4, line 12,   after "from" insert --insert--.
Col. 4, line 28,   "aritifical" should be
　　--artificial--.
Col. 6, line 27-28,   "additions" should be
　　--addition--.

Signed and Sealed this

Sixth Day of May 1980

[SEAL]

Attest:

SIDNEY A. DIAMOND

Attesting Officer　　Commissioner of Patents and Trademarks